US006872291B2

(12) United States Patent
Boyd et al.

(10) Patent No.: US 6,872,291 B2
(45) Date of Patent: Mar. 29, 2005

(54) METHOD AND DEVICE FOR DETECTING AND CONTROLLING THE LEVEL OF BIOLOGICAL CONTAMINANTS IN A COATING PROCESS

(75) Inventors: Donald W. Boyd, Cheswick, PA (US); Steven R. Zawacky, Pittsburgh, PA (US)

(73) Assignee: PPG Industries Ohio, Inc., Cleveland, OH (US)

(*) Notice: Subject to any disclaimer, the term of this patent is extended or adjusted under 35 U.S.C. 154(b) by 458 days.

(21) Appl. No.: 10/042,552

(22) Filed: Jan. 9, 2002

(65) Prior Publication Data

US 2002/0148738 A1 Oct. 17, 2002

Related U.S. Application Data

(60) Provisional application No. 60/260,487, filed on Jan. 9, 2001.

(51) Int. Cl.[7] ............................ C25D 13/00; C12M 1/34
(52) U.S. Cl. ......................... 204/472; 204/622; 435/34; 435/287.5; 436/133; 436/146
(58) Field of Search ................................ 204/472, 622, 204/489; 435/34, 287.5; 436/133, 146

(56) References Cited

U.S. PATENT DOCUMENTS

| 4,015,366 A | 4/1977 | Hall, III | 47/1 R |
| 4,220,858 A * | 9/1980 | Ikeguchi et al. | 250/34 |
| 4,304,996 A | 12/1981 | Blades | 250/373 |
| 4,637,987 A | 1/1987 | Minten et al. | 436/151 |
| 5,094,955 A | 3/1992 | Calandra et al. | 435/291 |
| 5,275,957 A | 1/1994 | Blades et al. | 436/133 |
| 5,518,895 A | 5/1996 | Thorpe et al. | 435/34 |
| 5,846,393 A | 12/1998 | Clarke et al. | 204/450 |
| 5,856,175 A | 1/1999 | Thorpe et al. | 435/287.5 |
| 5,858,769 A | 1/1999 | DiGuiseppi et al. | 435/287.3 |

FOREIGN PATENT DOCUMENTS

| EP | 732588 A2 * | 9/1996 |
| GB | 2 319 837 A | 11/1996 |
| WO | WO 91/05251 | 4/1991 |
| WO | WO 97/21096 | 6/1997 |

* cited by examiner

Primary Examiner—Kishor Mayekar
(74) Attorney, Agent, or Firm—Deborah M. Altman

(57) ABSTRACT

The presence of biological contaminants in a liquid coating composition is determined by measuring the carbon dioxide content of the atmosphere above the liquid and comparing the measured carbon dioxide level to a baseline carbon dioxide level. A biocide can be added to the liquid when the measured carbon dioxide level reaches a predetermined value to control the level of biological contaminants in the liquid coating composition.

51 Claims, 3 Drawing Sheets

METHOD AND DEVICE FOR DETECTING AND CONTROLLING THE LEVEL OF BIOLOGICAL CONTAMINANTS IN A COATING PROCESS

CROSS-REFERENCE TO RELATED APPLICATION

This application claims the benefits of U.S. patent application Ser. No. 60/260,487 filed Jan. 9, 2001, herein incorporated by reference in its entirety.

BACKGROUND OF THE INVENTION

1. Field of the Invention

The present invention relates generally to a method and device for detecting and/or treating biological contaminants in an electrodeposition coating process to provide electrocoated substrates having good smoothness and appearance.

2. Technical Considerations

Electrodeposition has become the primary method for applying corrosion-resistant primers in automotive applications. The electrodeposition process typically involves cleaning and/or pretreating an electroconductive substrate and then immersing the substrate into an electrocoating tank containing a bath of an aqueous electrocoating composition. The substrate serves as a charged electrode in an electrical circuit comprising the electrode and an oppositely charged counter-electrode. Sufficient current is applied between the electrodes to deposit a substantially continuous, adherent film of the electrocoating composition onto the surface of the substrate.

The electrocoated substrate is then conveyed into a rinsing operation where it is rinsed with an aqueous rinsing composition. Typical rinsing operations have multiple stages which can include closed loop spray and/or dip applications. In a spray rinse application, the electrocoated substrate exits the electrocoating tank and is conveyed over a rinse tank while an aqueous rinsing composition is spray applied by a spraying apparatus to the electrocoated surfaces of the substrate. Exces rinsing composition is permitted to drain from the substrate into the rinse tank below. The rinsing composition in the rinse tank is then recirculated back to the spraying apparatus for subsequent spray applications. In a dip rinse application, the electrocoated substrate is conveyed into a dip tank, where it is immersed in an aqueous rinsing composition, and is subsequently conveyed through one or more spray rinse applications as described above.

Recirculating the coating or rinsing compositions is both economically and environmentally desirable. However, the combination of organic nutrients, warmth, and recirculation in an aqueous coating system creates an environment conducive to bacterial and/or fungal growth. These biological contaminants, if left unchecked, could adversely affect the quality and appearance of the electrodeposited coating. Biological contaminants present in the coating and/or rinsing compositions can cause pH shifts, particulate "dirt" deposition, and biofouling, which may detrimentally affect the appearance of the coating and reduce system performance.

In order to combat such biofouling, biocides or biological inhibitors, such as ethylene glycol monobutyl ether, and the like, are typically added to liquids in the coating process, such as coating and/or rinsing compositions, when undesirable levels of microbial activity are detected. Since such materials can be environmentally undesirable as well as expensive, they are typically used sparingly and only when the measured biological activity begins to reach a point where it will adversely impact upon the coating process.

The presence and/or level of biological contaminants in a coating system, e.g., a coating composition, is typically measured by taking a sample of the coating composition and shipping the sample to a laboratory for analysis. However, this current practice has some undesirable limitations. For example, the analysis requires a certain degree of technical skill and is typically carried out at an off-site facility, requiring time for the sample to be taken, shipped, analyzed, and the results of the analysis returned. Therefore, the results obtained are not "real time" and the actual level of biological contamination present in the coating composition, and hence the correct amount of biocide to add, must be estimated based on the time at which the analyzed sample was actually taken. Further, such analysis is relatively costly to perform.

In non-coating related fields, non-analytical methods of measuring biological contaminants have been developed. For example, U.K. Patent Application GB 2,319,837 discloses a method of determining biological activity in a soil sample by placing the soil sample in a sample chamber linked to an indicator chamber, the sample chamber and indicator chamber being isolated from the ambient atmosphere. U.S. Pat. Nos. 5,094,955; 5,518,895; 5,856,175; and 5,858,769 disclose a device for detecting the presence of microorganisms in clinical specimens, such as blood or other body fluids, by culturing the specimens with a sterile growth medium in a transparent, sealed container. The presence of microorganisms in the sealed container is determined by measuring changes in the pH of the specimen or the production of $CO_2$ within the sealed container using a sensor affixed to the interior surface of the sealed container. However, such methods cannot be directly translated into the coating field, particularly the continuous electrodeposition coating field, since the coating tanks and rinse tanks in a conventional coating operation realistically cannot be isolated from the ambient atmosphere during the coating operation.

It would be desirable to provide a method and device for detecting and/or controlling the level of biological contaminants in coating and/or rinsing compositions of a coating process, and more particularly in electrodeposition coating and/or rinsing compositions, without adversely impacting upon operation of the coating and/or rinsing operations.

SUMMARY OF THE INVENTION

A method is provided for detecting and/or monitoring biological contamination in a coating liquid, such as a coating composition or a rinsing composition, comprising part of a coating process. The method comprises measuring a carbon dioxide content of at least a portion of the atmosphere adjacent the coating liquid. This measurement can be compared to a baseline carbon dioxide level of the ambient atmosphere to determine if elevated carbon dioxide levels are present adjacent, e.g., above, the liquid. In another embodiment, the measurement can be compared to a database of previous measurements correlating previously measured carbon dioxide levels for coating liquids to respective bacteria counts to estimate the degree of biological contamination. A biocide may be added to the liquid when the carbon dioxide content adjacent the liquid is a predetermined amount above the baseline level or when the estimated amount of biological contamination reaches a predetermined level.

Another method of detecting and controlling a level of biological contaminant in a coating liquid of a continuous coating process comprises measuring a carbon dioxide content of a portion of the atmosphere adjacent the liquid, determining a baseline carbon dioxide level in the area of the liquid, comparing the measured carbon dioxide level to the baseline carbon dioxide level, and determining biological contamination when the measured carbon dioxide level is a predetermined amount above the baseline level. A biocide can be added when biological contamination is determined.

A further method of detecting a biological contaminant in a coating liquid comprises obtaining at least a portion of the coating liquid, measuring a carbon dioxide content of the atmosphere adjacent the coating liquid, and comparing the measured carbon dioxide content to a database to estimate the level of biological contaminant in the coating liquid.

A coating system is also provided. The coating system comprises a container containing a liquid comprising part of a coating process, and at least one carbon dioxide sensor located adjacent the container. The container can be, for example, a coating tank, a rinsing tank, or a sample container containing a sample of the liquid.

An electrodeposition coating system is further provided. The electrodeposition coating system comprises a coating tank, a coating composition located in the coating tank, at least one rinse tank, a rinse composition located in the at least one rinse tank, and at least one carbon dioxide sensor located adjacent at least one of the coating tank and the rinse tank.

BRIEF DESCRIPTION OF THE DRAWINGS

The foregoing summary, as well as the following detailed description of the preferred embodiments, will be better understood when read in conjunction with the appended drawings, in which.

DESCRIPTION OF THE PREFERRED EMBODIMENTS

Figure 1:
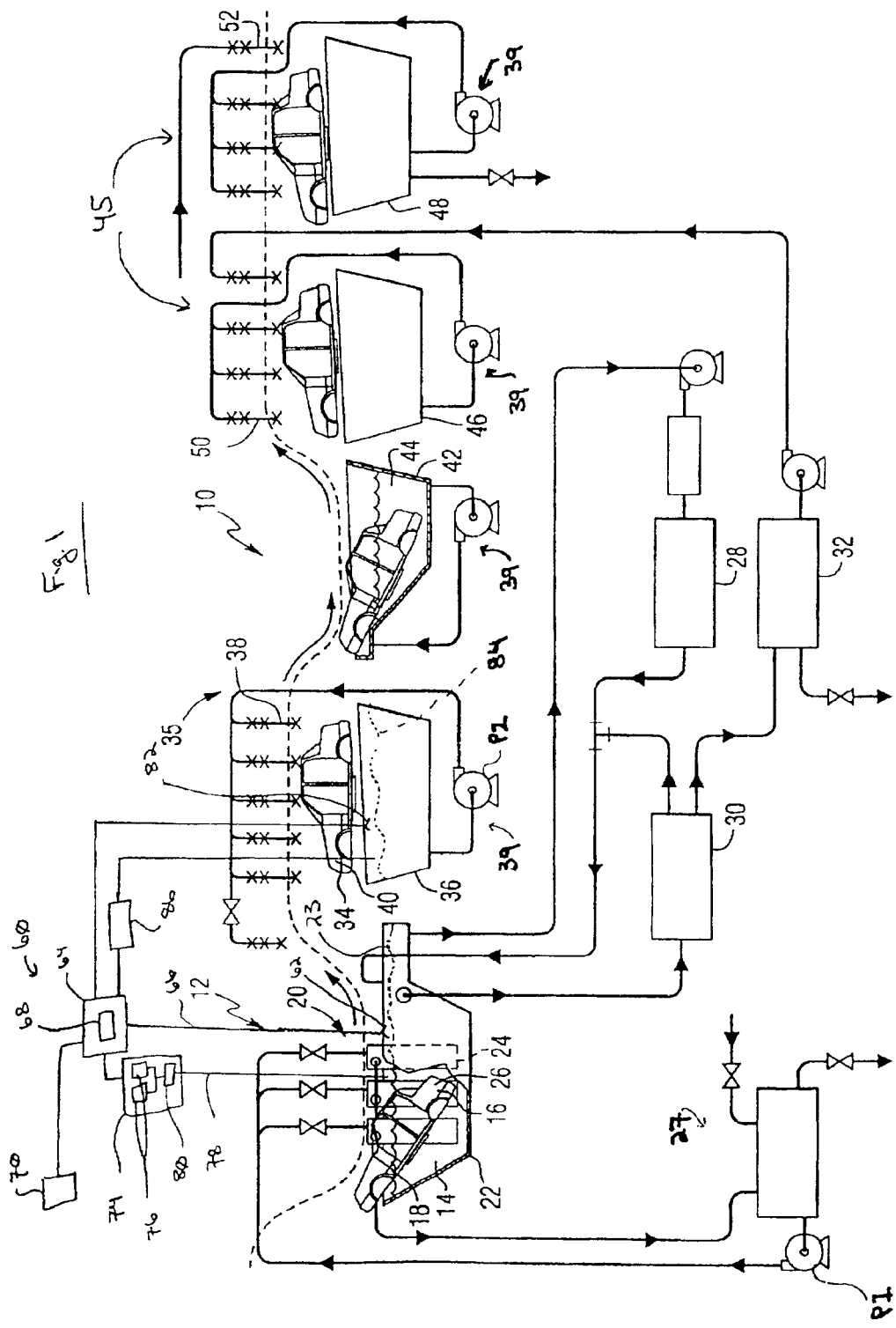
FIG. 1 is a schematic diagram of an exemplary process according to the present invention for applying an electrodepositable coating composition to an electroconductive substrate, rinsing the coated substrate with one or more rinsing compositions, and monitoring and/or controlling the level of biological contaminants in the coating and/or rinsing compositions.
Figure 2:
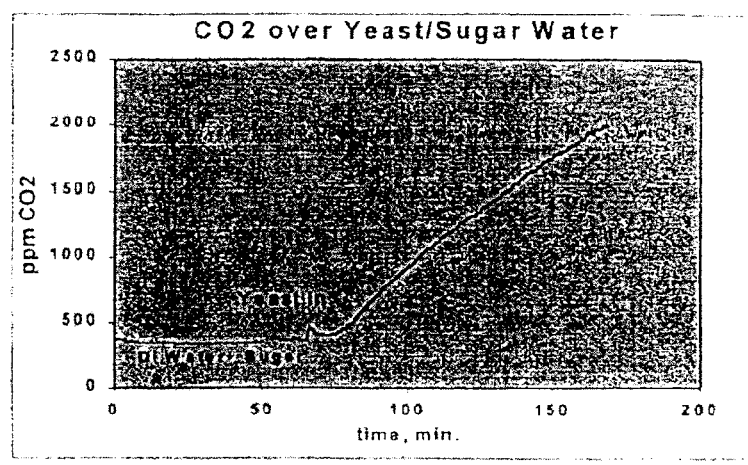
FIG. 2 is a graph of carbon dioxide level (ppm) versus time (mins.) for a mixture of yeast and sugar water.
Figure 3:
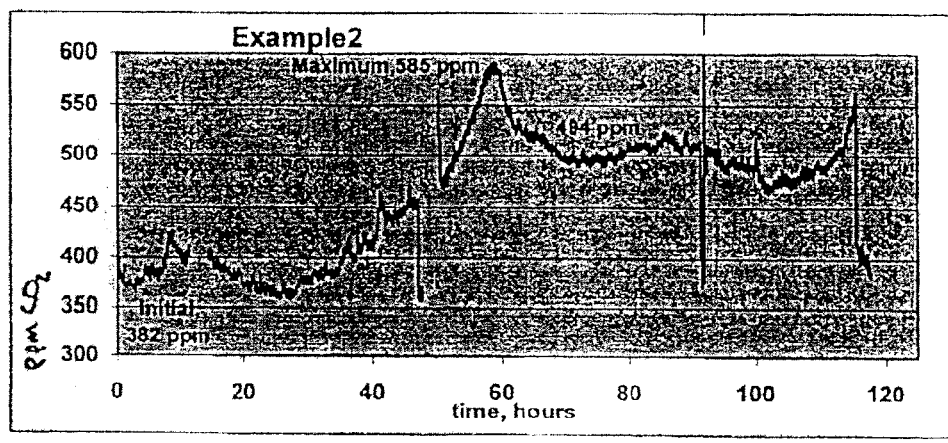
FIG. 3 is a graph of carbon dioxide level (ppm) versus time (hrs.) for a simulated coating liquid.

Other than in the operating examples, or where otherwise indicated, all numbers expressing physical characteristics, quantities of ingredients, reaction conditions, and so forth used in the specification and claims are to be understood as being modified in all instances by the term "about". Accordingly, unless indicated to the contrary, the numerical values set forth in the following specification and claims may vary depending upon the desired properties sought to be obtained. At the very least, and not as an attempt to limit the application of the doctrine of equivalents to the scope of the claims, each numerical value should at least be construed in light of the reported significant digits and by applying ordinary rounding techniques. Also, as used herein, the term "polymer" is meant to refer to oligomers, homopolymers, and copolymers. Molecular weight quantities used herein, whether Mn or Mw, are those determinable from gel permeation chromatography using polystyrene as a standard. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 5.5 to 10. As used herein, the term "coating liquid" refers generally to any liquid used in any part of the coating process, for example but not limited to pretreatment liquids (such as cleaning solutions, e.g., alkaline cleaners or acidic cleaners; or phosphating liquids), pigmented coating liquids, rinsing liquids, anolyte liquid, permeate, and the like. The coating liquid can be located in the continuous coating system (i.e., on-line) or can be in a holding tank or storage tank (i.e., off-line).

A method and device according to the present invention for detecting and/or controlling the level of biological contaminants in a coating liquid comprising part of a coating process will now be discussed with reference to an exemplary continuous automotive electrocoating and rinsing process. By "continuous process" is meant that the substrate is in continuous movement along an assembly line. However, it is to be understood that this exemplary continuous electrodeposition process is provided simply as one example of a process in which the invention can be practiced and the invention should not be considered as limited thereto. One skilled in the art would understand that the present invention could also be used, for example, in non-continuous, e.g., semi-continuous or indexing coating processes, or batch coating processes, or in non-electrophoretic coating processes. Additionally, while the following discussion is directed primarily to detecting the presence of biological contamination in an aqueous or solvent-borne electrodepositable coating composition and/or rinsing composition, it is to be understood that the invention could be practiced on any coating liquid at any point along the coating line, such as but not limited to pretreatment liquids, such as cleaning liquids or phosphating liquids, or with coating liquids located off-line, such as but not limited to water storage tanks, coating storage tanks, permeate tanks, and the like.

Referring now to FIG. 1, there is shown a schematic diagram of a portion of an exemplary continuous electrodeposition process (indicated generally as 10) for applying an electrodepositable coating composition to an electrically conductive substrate, for rinsing the coated substrate with one or more rinsing compositions, and for monitoring and/or controlling biological contamination in the coating and/or rinsing compositions according to the present invention.

Useful electrically conductive substrates that can be coated include those formed from metallic materials, for example ferrous metals such as iron, steel, and alloys thereof, non-ferrous metals such as aluminum, zinc, magnesium and alloys thereof, and combinations thereof. Preferably, the substrate is formed from cold-rolled steel, electrogalvanized steel such as hot-dipped electrogalvanized steel, hot-dipped galvanneal, or electro zinc-iron coated steel, aluminum or magnesium.

The electrically conductive substrates can be used as components to fabricate automotive vehicles, including but not limited to automobiles, trucks, and tractors. The electrically conductive substrates can have any shape, e.g., in the form of automotive body components, such as bodies (frames), hoods, doors, fenders, bumpers and/or trim, for automotive vehicles. A coating system incorporating the concepts of the present invention first will be discussed generally in the context of coating a metallic automobile body. One skilled in the art would understand that a coating process incorporating the present invention also is useful for coating non-automotive electrically conductive components.

The substrate is typically first cleaned to remove grease, dirt, or other extraneous matters. This is typically done by employing conventional cleaning procedures and materials. Such materials include mild or strong alkaline cleaners, such as or commercially available and conventionally used in metal treatment processes. Examples of alkaline cleaners include Chemkleen 163 and Chemkleen 177, both of which are available from PPG Industries, Pretreatment and Specialty Products. Such cleaners are generally followed and/or preceded by water rinse(s). Optionally, the metal surface may be rinsed with an aqueous acidic solution after cleaning with the alkaline cleaner and before contact with a subsequent coating composition. Examples of rinse solutions include mild or strong acidic cleaners, such as the dilute nitric acid solutions commercially available and conventionally used in metal treatment processes.

The metal substrate may also optionally be phosphated. Suitable phosphate conversion coating compositions may be any of those known in the art. Examples include zinc phosphate, iron phosphate, manganese phosphate, calcium phosphate, magnesium phosphate, cobalt phosphate, zinc-iron phosphate, zinc-manganese phosphate, zinc-calcium phosphate, and layers of other types, which may contain one or more multi-valent cations. Phosphating compositions are known to those skilled in the art and are described, for example, in U.S. Pat. Nos. 4,941,930; 5,238,506; and 5,653,790.

The substrate can also be contacted with one or more conventional passivating compositions to improve corrosion resistance. Such passivating compositions are typically dispersed or dissolved in a carrier medium, usually an aqueous medium. The passivating composition may be applied to the metal substrate by any known application techniques, such as by dipping or immersion, spraying, intermittent spraying, dipping followed by spraying, spraying followed by dipping, brushing, or by roll-coating. An exemplary passivating composition is described in U.S. Pat. No. 6,217,674.

Referring now to FIG. 1, in the electrodeposition portion 12 of the process 10, a coating liquid in the form of a liquid electrodepositable coating composition 14 is applied to a surface 16 of an electrically conductive automobile body 18 in a first step 20. The coating composition 14 can be applied, for example, by dipping the automobile body 18 into a container or bath 22 containing the liquid electrodepositable coating composition 14. The coating composition 14 has a top surface 23, the location of which top surface 23 in the bath 22 may vary between a maximum level and a minimum level depending upon the quantity of coating composition 14 in the bath 22 and whether the automobile body 18 is in or out of the bath 22. The liquid electrodepositable coating composition 14 can be applied to the surface 16 of the automobile body 18 by any suitable anionic or cationic electrodeposition process well known to those skilled in the art.

In a cationic electrodeposition process, for example, the liquid electrodepositable coating composition 14 is placed in contact with an electrically conductive anode 24 and an electrically conductive cathode (the electrically conductive surface 16 of the automobile body 18). Following contact with the liquid electrodepositable coating composition 14, an adherent film 26 of the coating composition 14 is deposited on the automobile body 18 when sufficient voltage is impressed and current is passed between the electrodes. The conditions under which electrodeposition is conducted are well understood by one of ordinary skill in the electrodeposition art and, therefore, will not be described in detail. The applied voltages can be varied and can be, for example, as low as 5 volts to as high as several thousand volts, but are typically between 50 and 500 volts. The current density is usually between 0.5 and 15 amperes per square foot and tends to decrease during electrodeposition indicating the formation of an insulating film.

Generally, any type of conventional electrodepositable or non-electrodepositable coating composition can be used in the practice of the invention. Preferably, the coating composition is electrodepositable. The electrodepositable coating composition 14 may be supplied as two components: (1) a clear resin feed, which can include one or more film-forming materials (ionic electrodepositable resins), crosslinking material(s), and any additional water-dispersible, non-pigmented components; and (2) a pigment paste, which can include one or more pigments, a water-dispersible grind resin which can be the same film-forming material as in the clear resin feed or a chemically different film-forming material such as those discussed below, and, optionally, additives such as wetting or dispersing aids. Electrodeposition bath components (1) and (2) may be dispersed in an aqueous medium which can include an admixture of water with coalescing solvents.

The electrodepositable coating composition can comprise one or more film-forming materials and crosslinking materials. Suitable film-forming materials include epoxy-functional film-forming materials, polyurethane film-forming materials, acrylic film-forming materials, polyester film-forming materials, and mixtures thereof. The amount of film-forming material in the electrodepositable composition generally ranges from about 50 to about 95 weight percent on a basis of total weight solids of the electrodepositable composition.

Suitable epoxy-functional materials may contain one or more epoxy or oxirane groups in the molecule, such as di- or polyglycidyl ethers of polyhydric alcohols. Preferably, the epoxy-functional material contains at least two epoxy groups per molecule. Useful polyglycidyl ethers of polyhydric alcohols can be formed by reacting epihalohydrins, such as epichlorohydrin, with polyhydric alcohols, such as dihydric alcohols, in the presence of an alkali condensation, and dehydrohalogenation catalyst such as sodium hydroxide or potassium hydroxide.

Such epoxy-functional materials can have an epoxy equivalent weight ranging from about 100 to about 2000, as measured by titration with perchloric acid using methyl violet as an indicator. Useful polyepoxides are disclosed in U.S. Pat. No. 5,820,987 at column 4, line 52 through column 6, line 59, which is incorporated herein by reference. Examples of suitable commercially available epoxy-functional materials are EPON® 828 and 880 epoxy resins, which are epoxy functional polyglycidyl ethers of bisphenol A prepared from bisphenol A and epichlorohydrin and are commercially available from Shell Chemical Company.

The epoxy-functional material can be reacted with amines to form cationic salt groups. Primary or secondary amines can be acidified after reaction with the epoxy groups to form amine salt groups. Tertiary amines can be acidified prior to reaction with the epoxy groups and after reaction with the epoxy groups form quaternary ammonium salt groups. Other useful cationic salt group formers include sulfides.

Suitable acrylic-functional materials include polymers derived from alkyl esters of acrylic acid and methacrylic acid such as are disclosed in U.S. Pat. Nos. 3,455,806 and 3,928,157, which are incorporated herein by reference.

Examples of film-forming resins suitable for anionic electrodeposition include base-solubilized, carboxylic acid-containing polymers such as the reaction product or adduct of a drying oil or semi-drying fatty acid ester with a dicarboxylic acid or anhydride; and the reaction product of a fatty acid ester, unsaturated acid or anhydride and any additional unsaturated modifying materials which are further reacted with polyol. Also suitable are at least partially neutralized interpolymers of hydroxy-alkyl esters of unsaturated carboxylic acids, unsaturated carboxylic acid and at least one other ethylenically unsaturated monomer. Other suitable electrodepositable resins comprise an alkyd-aminoplast vehicle, i.e., a vehicle containing an alkyd resin and an amine-aldehyde resin or mixed esters of a resinous polyol. These compositions are described in detail in U.S. Pat. No. 3,749,657 at column 9, lines 1–75 and column 10, lines 1–13, all of which are herein incorporated by reference. Other acid functional polymers can also be used, such as phosphatized polyepoxide or phosphatized acrylic polymers, which are well known to those skilled in the art.

Useful crosslinking materials comprise blocked or unblocked polyisocyanates including aromatic diisocyanates, such as p-phenylene diisocyanate, 4,4'-diphenylmethane diisocyanate, and 2,4- or 2,6-toluene diisocyanate; aliphatic diisocyanates, such as 1,4-tetramethylene diisocyanate and 1,6-hexamethylene diisocyanate or oligomers or trimers thereof; and cycloaliphatic diisocyanates, such as isophorone diisocyanate and 4,4'-methylene-bis (cyclohexyl isocyanate). Examples of suitable blocking agents for the polyisocyanates include lower aliphatic alcohols such as methanol, oximes such as methyl ethyl ketoxime, and lactams such as caprolactam. The amount of the crosslinking material in the electrodepositable coating composition generally ranges from about 5 to about 50 weight percent on a basis of total resin solids weight of the electrodepositable coating composition.

Generally, the electrodepositable coating composition 14 also comprises one or more pigments which can be incorporated in the form of a paste; water-dispersible, non-pigmented components such as surfactants and wetting agents; catalysts; film build additives; flatting agents; defoamers; microgels; pH control additives; and volatile materials such as water, organic solvents and low molecular weight acids, such as are described in U.S. Pat. No. 5,820, 987 at column 9, line 13 through column 10, line 27 (incorporated by reference herein).

Suitable pigments include iron oxides, strontium chromate, carbon black, coal dust, titanium dioxide, talc, barium sulfate, cadmium yellow, cadmium red, chromium yellow, and the like. The pigment content of the dispersion is usually expressed as a pigment-to-resin ratio. When pigment is employed, the pigment-to-resin ratio preferably is within the range of about 0.02 to 1:1. The other additives mentioned above are usually in the dispersion in amounts of about 0.01 to about 10 percent by weight, preferably about 0.1 to about 3 percent by weight based on weight of resin solids.

Useful solvents included in the coating composition 14, in addition to any provided with other coating components, include coalescing solvents such as hydrocarbons, alcohols, esters, ethers, glycol ethers, and ketones. Preferred coalescing solvents include alcohols, polyols, ethers, and ketones. Non-limiting examples of suitable solvents include isopropanol, butanol, 2-ethylhexanol, isophorone, 4-methoxy-2-pentanone, ethylene glycol, propylene glycol, and the monoethyl, monobutyl and monohexyl ethers of ethylene glycol. Generally, the amount of coalescing solvent ranges from 0.01 and 25 weight percent, and preferably from 0.05 to 5 percent by weight based on total weight of the electrodepositable coating composition.

Additionally, the coating composition also typically includes organic acids, such as acetic acid and lactic acid.

Examples of other useful electrodepositable coating compositions are disclosed in U.S. Pat. Nos. 4,891,111; 4,933, 056; and 5,760,107, which are incorporated herein by reference.

Suitable electrodepositable compositions preferably are in the form of an aqueous dispersion. As used herein, "dispersion" means a two-phase transparent, translucent or opaque resinous system in which the resin is in the dispersed phase and the water is in the continuous phase. The average particle size of the resinous phase is generally less than 1.0 micron and usually less than 0.5 micron, preferably less than 0.15 micron.

The concentration of the resinous phase in the aqueous medium is preferably at least 1 and usually ranges from 2 to 60 percent by weight based on total weight of the aqueous dispersion (electrodeposition bath). When the electrodepositable compositions are in the form of resin concentrates, they generally have a resin solids content of 20 to 60 percent by weight based on weight of the aqueous dispersion.

The thickness of the electrodepositable coating applied to the substrate can vary based upon such factors as the type of substrate and intended use of the substrate, i.e., the environment in which the substrate is to be placed and the nature of the contacting materials. Generally, the thickness of the electrodepositable coating applied to the substrate ranges from about 5 to about 50 micrometers, and more preferably about 12 to about 40 micrometers.

The coating composition in the bath 22 can be recycled in conventional manner, such as by a recycling system 27 having a pump P1 that prevents the solids of the coating composition from settling to the bottom of the bath 22. Further, the temperature of the electrodepositable coating composition 14 may be controlled by use of a heat exchanger 28 in flow communication with the bath 22 in any conventional manner, such as through pipes or conduits.

The electrodepositable coating composition 14 from the bath 22 also may be in flow communication with a conventional ultrafiltration system 30 to remove soluble impurities and the filtered material recycled to the electrodeposition bath 22. In the ultrafiltration system 30, the coating composition 14 flows over a membrane permeable to water and small particles, e.g., those less than about 1,000 Mw, such as salts. The ultrafiltrate or "permeate" 32, i.e., the portion of the coating composition which passes through the membrane, can be used in further rinsing operations and a portion of the permeate 32, e.g., about 20 weight percent, may be discarded. The "non-permeate" portion of the coating composition is directed back into the bath 22, e.g., through one or more conduits or pipes.

After conveying from the electrocoating bath 22, the electrocoated automobile body 34 is exposed to air to permit excess electrodeposited coating composition to drain from the interior cavities and surfaces of the automobile body 18 back into the bath 22. The electrocoated automobile body 34 is then conveyed to a rinsing process 35 for removing excess electrodepositable coating from the automobile body 34. The rinsing process can include one or more spray and/or dip rinsing operations, as desired. Preferably, the electrocoated automobile body 34 is conveyed over a spray rinse tank 36 where a first rinsing composition 38 is spray applied to the coated surfaces 40 of the electrocoated automobile body 34. The excess spray composition is permitted to drain into the rinse tank 36 below for recirculation, e.g., by a recirculation system 39 having a recirculation pump P2, for subsequent spray reapplication.

The rinsing composition 38 generally comprises water. Since it is typically recycled, it also can comprise minor amounts of electrodepositable coating composition, such as is described above, which have been rinsed from the coated body 34.

The spray rinse step can be followed by a dip rinse step in which the electrocoated automobile body 34 is conveyed to a rinse dip tank 42 and immersed in an aqueous rinsing composition 44 contained therein. The electrocoated automobile body 34 is then conveyed out of the rinse dip tank 42 and the excess rinsing composition is permitted to drain back into the tank 42 for reuse. The aqueous rinsing composition 44 used in the dip rinse tank 42 can have the same or different components from the first rinsing composition 38 discussed above, but preferably has the same components as the first rinsing composition 38.

The dip rinse step may be followed by one or more spray applied rinsing steps 45 as the electrocoated automobile body 34 is conveyed over subsequent spray rinsing tanks 46, 48, and aqueous rinsing compositions 50, 52 are spray applied as described above. Preferably, the drainage period for each rinsing step is at least one minute so that there is no standing water from the final rinsing composition. The temperature of the air during the drainage period preferably ranges from about 10° C. to about 40° C. One or more of the rinse tanks 48, 46, 42, and 36 may be in flow communication, such as through conduits or pipes, so that fresh rinsing composition added to one rinse tank, such as to the last rinse tank 48, flows, e.g., by pumps or gravity, to one or more of the upstream rinse tanks 46, 42, and/or 36.

A second electrodepositable coating may also be applied upon the surface of the dried electrocoat after the first electrocoat is rinsed as described above. The second electrodepositable coating can be applied in a manner similar to that discussed above for depositing the first electrodepositable coating.

The second electrodepositable coating can be the same or different from the first electrodepositable coating. For example, the individual components of the second electrodepositable coating, such as film-forming materials, can vary or the amounts of each component can vary, as desired. Suitable components for the second electro-depositable coating include those discussed above as suitable for the first electrodepositable coating. Preferably, the first electrodepositable coating comprises an epoxy-functional film-forming material and polyisocyanate crosslinking material to provide corrosion resistance, and the second electrodepositable coating comprises an acrylic or polyurethane, preferably polyurethane, film-forming material and polyisocyanate crosslinking material to provide chip resistance from impacts by stones and road debris as well as resistance to ultraviolet light that can cause photodegradation and loss of adhesion of the coating to the substrate.

During operation, one or more of the coating liquids, e.g., the pretreatment liquids, cleaning solutions, the electrodeposition coating composition 14 in the bath 22, or rinsing compositions 38, 44, 50, 52 in the rinse tanks 36, 42, 46 or 48 may become contaminated with one or more biological contaminants, such as bacteria or fungi, which could adversely impact upon the quality of the deposited and cured coating. Such bacteria or fungi are referred to generally herein as "biological contaminant(s)". It is believed the growth of such microorganisms is linked to the presence of organic acids, such as acetic or lactic acids, in the coating composition. However, these microorganisms have been shown to exist in very harsh natural environments.

In the past, such biological contamination would be confirmed and quantified by periodic sampling and analysis of the coating and/or rinsing compositions at a laboratory or off-site testing facility. Based on this analysis, a microorganism control agent or biocide would be added to the contaminated composition or the level of microorganism control agent already present in the composition would be manually adjusted. The drawbacks of such a conventional sampling and treating procedure have been discussed above.

However, the present invention provides a novel device and method for monitoring and/or controlling biological contamination in one or more of the coating liquids, e.g., the coating and/or rinse compositions. For this purpose, the present invention provides at least one biological contaminant detection and control system 60. The components of the system 60 will first be discussed with respect to monitoring electrocoat and/or rinse tanks and then an exemplary method of using the invention will be described. The system 60 includes at least one carbon dioxide sensor 62 which, as described below, may be positioned adjacent the coating liquid, e.g., the bath 22 in FIG. 1. For example, the sensor 62 can be positioned in the bath 22 but at a height such that it remains above, e.g., at about the same distance above, the top surface 23 of the coating composition 14 whether or not a substrate is immersed in the bath 22, e.g., less than about 5 feet (152 cm) above the top surface 23, preferably less than about 3 feet (91 cm), more preferably less than about 2 feet (61 cm), even more preferably less than about 1 foot (30 cm), and most preferably less than about 0.5 feet (15 cm).

Examples of suitable carbon dioxide sensors 62 include, but are not limited to, Q-TRAK™ sensors commercially available from Instrumentation Systems, Inc. of Monroeville, Pa., and Guardian™ 3000, MYCO$_2$, GASCARD™, GASBYTE™, and GUARDIAN™ PLUS INFRA-RED sensors commercially available from Edinburgh Sensors Ltd. of Livingston, Scotland.

In one embodiment, the carbon dioxide sensor 62 is in electronic communication for sending measurements of detected carbon dioxide levels to a control device 64. For example, the sensor 62 may be in communication with the control device 64 via a wire or cable 66, via a conventional wireless communication system (such as a conventional radiowave transmission and reception system), or in any other convenient manner.

The control device 64 may include a programmable computer system with appropriate software to permit the programming of start and stop times for sampling the carbon dioxide level, sample duration, sampling frequency, data logging frequency, and other parameters. A non-limiting example of one such system is the Q-TRAK™ IAQ system with TRAKPRO™ data analysis software commercially available from Instrumentation Systems, Inc. of Monroeville, Pa. The control device 64 may also include a display 68, such as a conventional liquid crystal display, and/or a printer for recording such data.

An audio and/or visual alarm 70 also may be part of or may be in electronic communication with the control device 64. The alarm 70 and/or control device 64 may be set or programmed to allow one or more alarm setpoints, e.g., carbon dioxide levels, to be established and/or changed. When the detected carbon dioxide level reaches a predetermined value, e.g., a predetermined amount above a baseline carbon dioxide level as described below, the alarm 70 can be activated to alert an operator.

Optionally, at least one biocide addition system 74 may be in operational communication with the control device 64. The addition system 74 may include one or more biocide storage tanks 76 in flow communication with the bath 22, such as by one or more pipes or conduits 78. The storage tanks 76 may contain the same or different biocides. The storage tanks 76 may be in flow communication with a selector device 80, such as a directional control valve, in operational communication with the control device 64 so that the biocide from one or more of the storage tanks 76 can be selectively directed into the bath 22. As discussed in further detail below, biocide can be added to the coating composition in the bath 22 either manually or automatically based upon the measured levels of carbon dioxide, which is an indication of the level of biological contamination in the tank.

One or more other such detection and control systems 60 as described above can be provided for one or more of the rinse tanks 36, 42, 46 or 48. Alternatively, as shown in FIG. 1, another carbon dioxide sensor 82 can be located adjacent a selected one of the rinse tanks, e.g., tank 36, and in electronic communication with the control device 64. The sensor 82 may be positioned proximate the rinse tank 36 at a height such that it remains adjacent to but above a top surface 84 of the rinsing composition 38. For example, the sensor 82 may be positioned below the upper lip of the rinse tank 36 but above the top surface 84 of the rinsing composition 38. Another biocide addition system 86, similar to that described above, optionally can be in electronic communication with the control device 64 and in flow communication with one or more rinse tanks, such as rinse tank 36.

An exemplary method of practicing the invention will now be discussed with particular reference to monitoring and/or controlling the level of biological contaminants in the coating composition 14 located in the bath 22.

As will be appreciated by one of ordinary skill in the art, the ambient carbon dioxide level, i.e., the amount of carbon dioxide in the ambient atmosphere at a location along a coating process, can vary during a normal operating day. For example, the ambient carbon dioxide level would be expected to vary between daytime hours when workers are present and nighttime when the workers have gone home. Further, the ambient carbon dioxide level could vary between weekdays and the weekend. Other factors that could affect the ambient carbon dioxide level include the time of year, whether the heating or air conditioning systems are in operation, etc.

Therefore, in the preferred practice of the invention, a baseline carbon dioxide level above or adjacent the area of the bath 22 is first obtained. By "baseline carbon dioxide level" is meant the ambient carbon dioxide in the vicinity of the bath 22 measured over a period of time to establish how the ambient carbon dioxide level at the bath 22 varies with time in the absence of biological contamination in the coating composition. The baseline carbon dioxide level can be determined by measuring the ambient carbon dioxide level above or adjacent the bath 22 at selected intervals, e.g., every sixty seconds, preferably every thirty seconds, and more preferably every five to six seconds, for a period of time, for example, for about one day, preferably about one week, more preferably greater than one week, to determine how the ambient carbon dioxide level at that location of the bath 22 changes with time during the selected period of time. A baseline graph or chart plotting the measured ambient carbon dioxide level with respect to selected reference times, e.g., diurnal variations in the ambient carbon dioxide level, could then be made. Alternatively, this data can be stored electronically, e.g., in a computer memory in the control device 64. These baseline carbon dioxide level measurements can be made automatically, e.g., using a conventional carbon dioxide measuring system, or could be done manually by a worker using a hand-held carbon dioxide measuring device.

When this baseline carbon dioxide level has been obtained for the particular location to be monitored, the presence of biological contaminants in the coating composition 14 can be determined by monitoring the atmosphere above, e.g., adjacent, the top surface 23 of the coating composition 14 with the carbon dioxide sensor 62 and comparing this measured carbon dioxide level to the baseline carbon dioxide level for a same or substantially similar reference time. By "reference time" is meant a particular time of day for a particular day of the week. For example, if the carbon dioxide level above the coating composition 14 is measured by the carbon dioxide sensor 62 at 3:45 pm on Wednesday (i.e., the reference time is 3:45 pm Wednesday), this measured carbon dioxide level should be compared to a baseline level previously determined as described above for a same or similar reference time (at or about 3:45 on a Wednesday). By comparing the measured carbon dioxide level to the baseline level for a substantially similar reference time, i.e., a baseline level previously measured at a similar time of day on a similar day of the week, normal fluctuations in the ambient carbon dioxide level can be accounted for even though the baseline level may have been established weeks before the measurement of the carbon dioxide level adjacent the coating composition is made. For example, it would not be recommended to compare a measured carbon dioxide level taken at 3:45 pm on a Wednesday to a baseline level previously determined for 11:00 am on a Sunday since the amount of ambient carbon dioxide on a weekend, when there are no workers around and the climate control system may have been turned off, would be expected to be different than that for a normal work day.

If the measured carbon dioxide level is substantially above the baseline value for the same or similar reference time, this is an indication of biological activity in the coating composition 14. By "substantially above" is meant greater than one standard derivation with respect to the previously recorded baseline level of carbon dioxide, preferably greater than two standard derivations, more preferably two to three standard derivations, and most preferably greater than three standard derivations. Biocide should then be added to the coating composition. Alternatively, rather than using standard deviation as a reference, as described in more detail below a particular mathematical difference between the measured amount of carbon dioxide and the baseline level can be used to define when biocide should be added.

A "setpoint" measured carbon dioxide level can be established to define a measured carbon dioxide level at which biocide should be added to the coating composition. For example, the setpoint can be defined when the carbon dioxide level measured by the sensor 62 differs from the previously determined baseline value for the substantially same reference time by more than three standard derivations, as described above. Alternatively, a numerical setpoint can be defined. For example, the setpoint can be defined as a difference between the measured carbon dioxide level and the baseline carbon dioxide level at a substantially similar reference time of a selected amount, e.g., greater than or equal to 100 ppm, preferably greater than or equal to 50 ppm, more preferably greater than or equal to 25 ppm. For example, if a carbon dioxide level of 340 ppm is measured by the sensor 62 at a reference time of 2:15 pm on Saturday and the previously established baseline value for at or about 2:15 pm on a Saturday was 290 ppm carbon dioxide, this is a difference of 50 ppm carbon dioxide. If the setpoint has been established as 50 ppm, this would mean that biocide should be added to the coating composition. The measurement of the carbon dioxide level adjacent the coating composition is believed to be a more direct and immediate indicator of biological activity than the previous testing methods described above.

The measurement of the carbon dioxide level adjacent the coating composition 14 can be performed manually, e.g., by a worker reading the display 68 or by a worker taking carbon dioxide level readings using a conventional hand-held carbon dioxide sensor. This measured carbon dioxide level can then be compared to the previously established baseline level for a same or similar reference time plotted on a table or graph previously prepared as described above. Alternatively, the comparison of the measured carbon dioxide level to the baseline carbon dioxide level can be performed automatically by the control device 64 based on the previously generated baseline values which can be stored in a database. When the setpoint is reached, e.g., when the sensor 62 detects a carbon dioxide level in the atmosphere above the coating composition 14 which is more than the a predetermined amount above the baseline value for a same or substantially similar reference time, e.g., greater than three standard derivations, or greater than 100 ppm, the control device 64 can direct the alarm 70 to sound to alert workers to manually add a predetermined amount of biocide to the coating composition 14. Alternatively, this biocide addition can be automatically controlled. For example, when the setpoint is reached, the control device 64 can activate the biocide addition system 74 to automatically add a predetermined amount of one or more of the biocides from one or more of the biocide storage tanks 76 to the coating composition 14.

The amount of biocide added to the coating composition depends on several factors, such as but not limited to how high the setpoint is defined, i.e., how high the biological contamination is before biocide is added, the type of biocide used, the total volume of coating composition, and the temperature of the coating composition, just to name a few. One skilled in the art can readily determine the amount of biocide to be added based on prior experience in combating biological contamination in the coating composition 14 and/or by routine experimentation. Alternatively, the amount of biocide can be determined based on the manufacturer's recommended dosage for the particular coating composition 14 under the particular coating parameters in use.

In addition to detecting and controlling biological contamination in the coating composition 14 as described above, biological contamination in one or more of the rinse tanks 36, 42, 46 or 48 also can be monitored, e.g., continuously monitored, and controlled in similar manner as described above for the coating composition. For example, as shown in FIG. 1, the other carbon dioxide sensor 82 can be used to monitor the carbon dioxide level adjacent the rinse tank 36. This measured carbon dioxide level can be compared to a baseline value determined as described above for the substantially same reference time. The other biocide addition system 86 can be used to treat the rinsing composition 38 in similar manner as described above for the coating composition.

In an alternative embodiment of the invention, rather than using a detection and control system 60 as described above, a selected amount of the coating liquid to be tested, such as of the coating composition 14 from the bath 22 or of the rinsing composition from one of the rinse tanks, may be taken and placed in a sample container which may be sealed to prevent contamination of the sample by the outside environment. A conventional carbon dioxide sensor can be used to measure the carbon dioxide level in the container at a predetermined distance above the sample liquid. This carbon dioxide level can be compared to a previously established baseline value to determine a difference in carbon dioxide level. The liquid can be evaluated periodically by sampling the liquid, placing the liquid sample in the sample container, measuring the carbon dioxide level in the sample container above the liquid, comparing the measured carbon dioxide level to a previously determined baseline level for substantially the same reference time, and, optionally, adding a biocide to the liquid in the coating operation when a selected setpoint is reached.

As will be appreciated by one of ordinary skill in the art, the baseline levels should be updated periodically, such as when new equipment is added to the coating facility, when the seasons change, when the coating facility is renovated, etc.

Alternatively, rather than establishing a baseline carbon dioxide level as described above, a reference carbon dioxide sensor (not shown) can be placed at or near the coating location monitored by the system 60 to monitor ambient carbon dioxide levels at or near the coating location. The reference sensor can be placed in electronic communication with the control device 64 to continuously monitor the ambient carbon dioxide level at the coating location. Thus, when a measurement of the carbon dioxide level above the coating liquid is taken by the sensor 62, a simultaneous baseline or reference level can be taken by the reference sensor and the two values (the measured value above the coating liquid and the reference or baseline value from the reference sensor) compared in similar manner as described above.

In a still further embodiment, a sample of the coating liquid to be tested, e.g., such as the coating composition 14 from the bath 22, may be taken and placed in a container. The top of the container may be covered and/or sealed and then the level of carbon dioxide in the headspace between the top of the liquid and the bottom of the cover measured. Upon measurement of the carbon dioxide level, the coating liquid can be tested in conventional manner to determine the amount of bacterial contamination, e.g., the "bacteria count", of the coating liquid. This bacteria count can then be correlated or equated to the recorded carbon dioxide level in the headspace of the container. In similar manner, a database of the level of $CO_2$ measured in the headspace versus the bacteria count in the coating liquid can be generated for other coating liquid samples having varying degrees of biological contamination. After formation of the database, when contamination is to be determined in a coating liquid, a sample of the coating liquid can be removed and placed in a sample container and the level of carbon dioxide in the headspace measured. This measured carbon dioxide level can then be compared or correlated to the previously measured carbon dioxide levels and their respective bacteria counts to determine an estimated bacteria count for the sampled coating liquid. Based upon this determined value, a selected amount of biocide can then be added to the coating liquid.

The present invention will be described further by reference to the following examples. The following examples are merely illustrative of the general concept of the invention and are not intended to be limiting. Unless otherwise indicated, all parts and percentages in the following examples, as well as throughout the specification, are by weight.

EXAMPLE 1

This example illustrates the feasibility of measuring the carbon dioxide level of the atmosphere above a liquid in a system which is not isolated from the ambient atmosphere.

A one gallon (3.8 liters) plastic paint container, 8.0 inches (20.3 cm) high with a diameter of 6.25 inches (15.9 cm), was used as a sample containment vessel. A growth medium of 10.66 g of Domino® granulated sugar dissolved in 1304.0 g of deionized water was added to the containment vessel. The growth medium occupied about one third of the vessel volume. The remainder of the vessel volume was ambient air. A lid having a 0.25 inch (0.64 cm) hole with a piece of Tygon™ tubing ("sample tubing") of 0.25 inch (0.64 cm) diameter and a length of about 50 inches (105 cm) attached thereto was loosely placed over the top of the vessel, i.e., the interior of the vessel was not isolated from the ambient atmosphere.

A Guardian™ Plus Infra-Red Gas Monitor System, commercially available from Edinburgh Instruments of Livingston, Scotland, was connected to the other end of the sample tube. The monitor system removed approximately 100 standard cubic feet per hour (scfh) (2830 liters per hour) of the atmosphere above the growth medium, which was replaced with ambient atmosphere flowing into the loosely closed vessel. This resulted in a turnover of the "headspace", i.e., the space between the bottom of the lid and the top of the liquid, every 5 to 7 minutes. The carbon dioxide level was monitored at about 0.5 min. to about 2 min. intervals using a Datalogger MultiMeter device, commercially available from Extech of Waltham, Mass. The carbon dioxide level in the ambient atmosphere adjacent (outside) the container was simultaneously monitored and the ambient carbon dioxide level (baseline level) remained between about 350 ppm to about 385 ppm during the experiment.

Next, 0.682 g of activated dry yeast (commercially available from Fleischmann's) was introduced into the growth medium in the vessel. After 2–3 minutes, the measured carbon dioxide level from the headspace began to rise above the ambient carbon dioxide level (baseline level), indicating the presence of biological growth in the medium. This growth was subsequently confirmed by observation of an increased quantity of yeast sedimented in the container. At a measured carbon dioxide level of 2000 ppm in the headspace, the experiment was terminated. A graph of measured carbon dioxide level (ppm) in the headspace versus time (minutes) for this experiment is shown in FIG. 2.

This experiment established that the experimental system described above was capable of detecting increasing levels of carbon dioxide generated by biological growth in a liquid composition which was not isolated from the ambient atmosphere.

EXAMPLE 2

The experimental system described in Example 1 was next used to determine if biological contamination could be detected in a liquid including components found in a typical electrocoating system.

Since, as discussed above, the growth of bacteria, such as *Pseudomonas Aeruginosa*, in conventional electrocoating systems is believed linked to the level of organic acids, such as acetic acid and lactic acid, in the coating composition, a "sample coating medium" containing acetic acid and lactic acid to simulate a coating composition was prepared for testing. The sample medium comprised a mixture of dihydrogen phosphate (commercially available from Aldrich Chemical Co.), sodium ammonium phosphate (commercially available from Fisher), L-(+)-Lactic acid (90%, commercially available from Arcos Company), and acetic acid (glacial, commercially available from Aldrich Chemical Company). These materials were mixed into distilled water to give the overall composition set forth in Table 1 below (all values are in ppm). The pH of the mixture was adjusted to 7.0 with aqueous potassium hydroxide (commercially available from Fisher Scientific).

TABLE 1

| | |
|---|---|
| $Na^+$ | 124.4 |
| $NH_4^+$ | 129.4 |
| $K^+$ | 136.3 |
| Phosphate | 580.0 |
| Acetate | 92.9 |
| Lactate | 27.4 |

1001.8 grams of this sample coating medium were placed in the empty containment vessel and the lid loosely placed over the vessel. An initial carbon dioxide level of 381±7 ppm was recorded for the atmosphere in the headspace above the liquid. The ambient level of carbon dioxide in the atmosphere outside the vessel was simultaneously monitored and remained about 360 ppm to about 391 ppm during the course of the experiment. No efforts were made to sterilize the medium or to exclude airborne bacteria.

One hundred grams of deionized water was then added to the container and no significant change in carbon dioxide level was noted (383±4 ppm). After about thirty minutes, an additional two hundred and fifty grams of deionized water was added with no appreciable change in carbon dioxide level (382±4 ppm). The carbon dioxide level in the headspace was continuously monitored as described in Example 1 and the results are shown in FIG. 3.

As shown in FIG. 3, there was an initial increase in carbon dioxide level in the headspace to over 400 ppm after about ten hours and then a decrease back to background (baseline) levels (about 359±2 ppm) after about twenty-four hours. It is believed that this initial increase was not due to bacterial growth but rather to fluctuations in the ambient air volume (the period in question occurred over a weekend when air conditioning and circulating systems were minimized). The measured carbon dioxide level in the headspace then grew rapidly to a maximum of about 585±3 ppm, indicating bacterial growth, which was subsequently confirmed by conventional analysis. The bacterial contamination was believed due to contamination by airborne bacteria. The measured carbon dioxide level then subsided to a substantially steady level of about 500 ppm. After about 120 hours, a biological analysis of a sample of the liquid was conducted which showed 4,000,000 colony forming units (cfu) using a conventional APHA Aerobic Plate Analysis method conducted by Microbac Laboratories, Inc. of Pittsburgh, Pa. The bacteria identified were *Psuedomonas Aeruginosa* and *Burkholderia Cepacia*.

EXAMPLE 3

This example illustrates the detection of biological contamination in a liquid which had been purposely contaminated with a sample of an electrodeposition coating composition which was known to be biologically contaminated.

A "sample medium" similar to that of Example 2 containing acetic acid and lactic acid was prepared from a mixture of dihydrogen phosphate (commercially available from Aldrich Chemical Co.), sodium ammonium phosphate (commercially available from Fisher), L-(+)-Lactic acid (90%, commercially available from Arcos Company), and acetic acid (glacial, commercially available from Aldrich Chemical Company). The pH of the mixture was adjusted to 7.0 with aqueous potassium hydroxide (commercially available from Fisher Scientific). The resulting mixture contained the following components (all values are in ppm):

TABLE 2

| | |
|---|---|
| $Na^+$ | 140.4 |
| $NH_4^+$ | 127.3 |
| $K^+$ | 127.3 |
| Phosphate | 580.0 |
| Acetate | 97.8 |
| Lactate | 23.5 |

Figure 4:
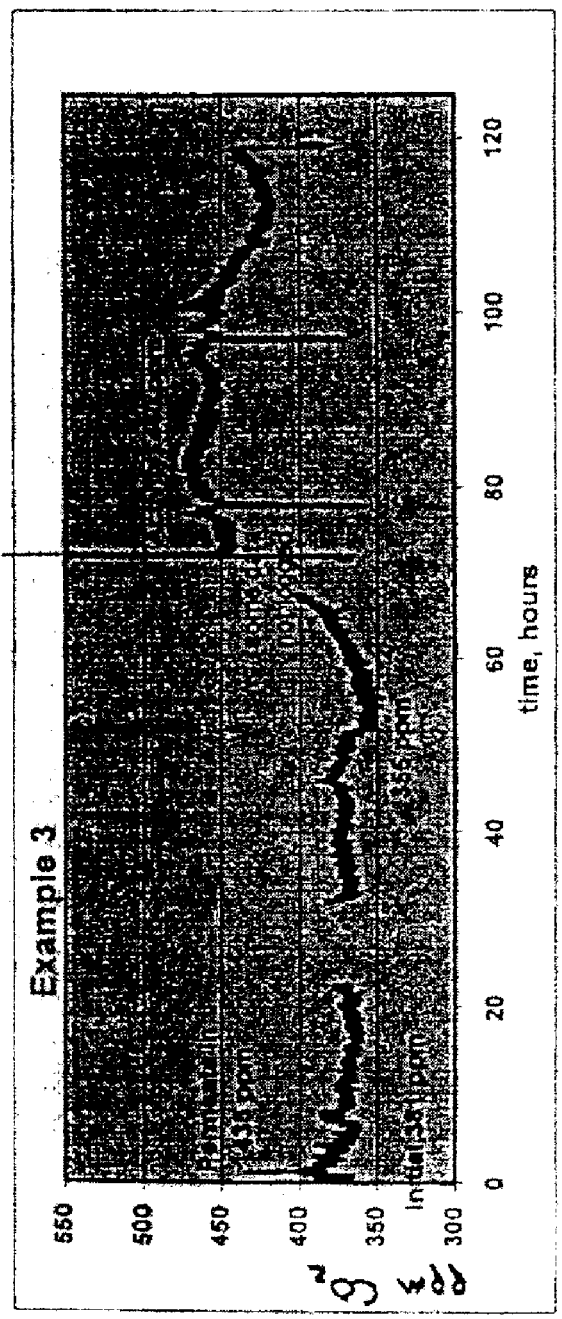
FIG. 4 is a graph of carbon dioxide level (ppm) versus time (hrs.) for a simulated coating liquid into which a biologically contaminated electrocoat permeate has been added.

One thousand grams of this sample medium were placed in the empty containment vessel and an initial carbon dioxide level of 381±7 ppm was recorded for the atmosphere in the headspace above the liquid after about 15 minutes. One hundred grams of deionized water was then added to the container and no significant change in carbon dioxide level was noted (the carbon dioxide level recorded was 383±4 ppm). The carbon dioxide level was monitored as described above and the results are shown in FIG. 4 (some data not logged).

One hundred and fifty-eight grams of an electrocoat permeate from a commercial electrocoat operation known to be heavily contaminated (i.e., 30 million cfu using APHA Aerobic Plate Analysis) with *Pseudomonos Aeruginosa* was then added to the liquid. An initial increase in carbon dioxide level in the headspace to 435 ppm was observed followed by a return to background carbon dioxide levels.

After about sixty hours, the carbon dioxide level in the headspace began to rise and after about twenty more hours the carbon dioxide level reached a steady state value of 440 ppm to about 460 ppm. The levels of carbon dioxide in the ambient atmosphere outside the vessel were monitored and were about 371 ppm to about 389 during the experiment, significantly lower than the measured carbon dioxide levels in the headspace of the containment vessel.

The liquid was then analyzed by a conventional test (APHA Aerobic Plate Analysis by Microbac Laboratories, Inc. of Pittsburgh, Pa.) and 21,000,000 cfu were detected. The bacteria were identified as *Pseudomonos Aeruginosa*. The level of bacterial contamination in the intentionally contaminated liquid of Example 3 was high, as was that of the liquid of Example 2, establishing that biological activity in the electrocoat contaminated liquid can be detected by monitoring the carbon dioxide level in the atmosphere above the liquid.

As will be appreciated by one of ordinary skill in the art, there are many different strains of bacteria that can potentially contaminate a coating liquid. Each of these strains may have different growth and respiratory capabilities that can affect the total amount of carbon dioxide generated by the bacteria.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims and any and all equivalents thereof.

What is claimed is:

1. A method of detecting biological contamination in a liquid comprising part of a coating process, the method comprising the steps of:
    (a) measuring a carbon dioxide content of at least a portion of the atmosphere adjacent the liquid;
    (b) determining a baseline level of carbon dioxide in the area of the liquid;
    (c) comparing the measured carbon dioxide level from step (a) to the baseline carbon dioxide level from step (b) to establish biological contamination when the measured carbon dioxide level is greater than a predetermined amount above the baseline carbon dioxide level; and
    (d) adding a biocide to the liquid when the measured carbon dioxide content is at or above the predetermined amount above the baseline carbon dioxide level.

2. The method according to claim 1, wherein the liquid comprises a biological contaminant.

3. The method according to claim 1, wherein the liquid comprises a coating material.

4. The method according to claim 1, wherein the liquid comprises water.

5. The method according to claim 1, wherein the liquid comprises part of a continuous electrodeposition coating process.

6. The method according to claim 1, wherein the liquid is a coating composition located in a coating tank.

7. The method according to claim 6, wherein the coating composition is an electrodepositable coating composition.

8. The method according to claim 6, wherein the coating composition is waterborne.

9. The method according to claim 6, wherein the coating composition is a basecoating composition.

10. The method according to claim 6, wherein the coating composition is a topcoating composition.

11. The method according to claim 6, wherein the measuring step (a) includes measuring the carbon dioxide content of the atmosphere above the liquid in the coating tank.

12. The method according to claim 1, wherein the liquid is an aqueous rinse composition located in a rinse tank.

13. The method according to claim 12, wherein the measuring step (a) includes measuring the carbon dioxide content of the atmosphere above the liquid in the rinse tank.

14. The method according to claim 1, wherein the adding step (d) is automatically controlled.

15. The method according to claim 1, further comprising the step of:
    (e) selecting a measured carbon dioxide level above the baseline level as a biocide addition setpoint.

16. The method according to claim 15, further comprising the step of:
    (f) determining an amount of biocide to be added from step (e).

17. The method according to claim 16, further comprising the step of:
(g) adding the determined amount of biocide to the liquid when the carbon dioxide level reaches the setpoint.

18. The method according to claim 17, wherein the adding step (g) is automatically controlled.

19. A method of detecting and controlling a level of biological contaminant in a continuous coating process comprising a liquid, comprising the steps of:
(a) measuring a carbon dioxide content of a portion of the atmosphere adjacent the liquid;
(b) determining a baseline carbon dioxide level in the area of the liquid;
(c) comparing the measured carbon dioxide level to the baseline carbon dioxide level; and
(d) adding a biocide to the liquid when the measured carbon dioxide level is a predetermined amount above the baseline level.

20. The method according to claim 19, wherein the liquid comprises a coating material.

21. The method according to claim 19, wherein the liquid comprises part of a continuous electrodeposition coating process.

22. The method according to claim 19, wherein the liquid is a coating composition located in a coating tank.

23. The method according to claim 22, wherein the coating composition is an electrodepositable coating composition.

24. The method according to claim 22, wherein the measuring step (a) includes measuring the carbon dioxide content of the atmosphere above the coating tank.

25. The method according to claim 24, wherein the adding step (d) is automatically controlled.

26. The method according to claim 25, further comprising the step of:
(e) selecting a difference in carbon dioxide level between the measured level and the baseline level as a biocide addition setpoint.

27. The method according to claim 26, further comprising the step of:
(f) adding biocide to the liquid when the measured carbon dioxide level reaches the setpoint.

28. The method according to claim 27, wherein the adding step (f) is automatically controlled.

29. The method according to claim 19, wherein the measuring step (a) includes positioning at least one carbon dioxide sensor adjacent the liquid.

30. The method according to claim 29, including electronically connecting the carbon dioxide sensor with at least one control device.

31. The method according to claim 30, including electronically connecting the control device with at least one biocide addition device, with the biocide addition device in flow communication with the liquid, and with the control device configured to automatically activate the biocide addition device to deliver a predetermined amount of biocide to the liquid when the sensor senses the predetermined level of carbon dioxide.

32. The method according to claim 19, wherein the liquid is a rinse composition located in a rinse tank.

33. The method according to claim 32, wherein the measuring step (a) includes measuring the carbon dioxide content of the atmosphere above the rinse composition in the rinse tank.

34. The method according to claim 33, wherein the adding step (d) is automatically controlled.

35. A coating system, comprising:
a container for containing a liquid comprising part of a coating process;
at least one carbon dioxide sensor located adjacent the container;
a control device in electronic communication with the at least one sensor; and
at least one biocide addition device in electronic communication with the control device and in flow communication with the container.

36. The coating system according to claim 35, wherein the coating system is an automotive coating system.

37. The coating system according to claim 35, wherein the coating system comprises a continuous electrodeposition coating system.

38. The coating system according to claim 35, wherein the liquid is a coating composition and the container is a coating tank.

39. The coating system according to claim 38, wherein the coating composition is an electrodepositable coating composition.

40. The coating system according to claim 38, wherein the coating composition is waterborne.

41. The coating system according to claim 38, wherein the coating composition is a basecoating composition.

42. The coating system according to claim 38, wherein the coating composition is a topcoating composition.

43. The coating system according to claim 35, wherein the liquid is a rinse composition and the container is a rinse tank.

44. An electrodeposition coating system, comprising:
a coating tank;
at least one rinse tank;
at least one carbon dioxide sensor located adjacent at least one of the coating tank and the rinse tank;
at least one control device in electronic communication with the at least one sensor; and
at least one biocide addition device in electronic communication with the control device and configured to add biocide to at least one of the coating tank and the rinse tank.

45. A method of detecting a biological contaminant in a coating process, comprising the steps of:
(a) obtaining a sample of a liquid comprising part of a coating process;
(b) measuring a carbon dioxide content of at least a portion of the atmosphere adjacent the sample;
(c) determining a baseline carbon dioxide level;
(d) determining biological contamination in the liquid by comparing the measured carbon dioxide level to the baseline level; and
(e) adding a biocide to the liquid when the measured carbon dioxide content is at or above a predetermined level with respect to the baseline level after step (d).

46. A method of determining biological contamination in a liquid comprising part of a coating process, comprising the steps of:
(a) determining a baseline carbon dioxide level in the vicinity of the liquid;
(b) measuring a carbon dioxide level of at least a portion of the atmosphere adjacent the liquid;
(c) comparing the measured carbon dioxide level to the baseline carbon dioxide level; and
(d) determining biological contamination when the measured carbon dioxide level is a selected amount above the baseline level;

wherein the liquid is a container and step (a) comprises measuring an ambient carbon dioxide level adjacent the container for a period of time to determine changes in ambient carbon dioxide level over a plurality of reference times, and wherein step (d) comprises:

(e) measuring the carbon dioxide level adjacent the liquid;

(f) comparing the measured carbon dioxide level from step (e) to the baseline carbon dioxide level for a substantially similar reference time;

(g) determining biological contamination in the liquid when the measured carbon dioxide level from step (e) is greater than the baseline carbon dioxide level for a substantially similar reference time; and (h) adding a biocide to the liquid when biological contamination is determined.

47. The method according to claim 46, wherein the ambient carbon dioxide level adjacent the container is measured to provide a diurnal ambient carbon dioxide level.

48. The method according to claim 46, including adding the biocide when the measured carbon dioxide level is greater than 100 ppm above the baseline carbon dioxide level for a substantially similar reference time.

49. The method according to claim 46, including adding the biocide when the measured carbon dioxide level is greater than three standard derivations above the baseline carbon dioxide level for a substantially similar reference time.

50. A method of detecting a biological contaminant in a coating liquid, comprising the steps of:

obtaining sample of the coating liquid;

measuring a carbon dioxide content of the atmosphere adjacent the coating liquid sample;

comparing the measured carbon dioxide content of the sample to a database to estimate the level of biological contaminant in the coating liquid; and adding a biocide to the coating liquid when the measured carbon dioxide content of the sample is at or above an predetermined level.

51. The method according to claim 50, wherein the database is formed by:

obtaining a plurality of samples of coating liquids having different levels of biological contaminants;

measuring the carbon dioxide content of at least a portion of the atmosphere adjacent the samples;

determining a level of biological contamination in each of the coating liquids; and correlating the measured carbon dioxide content to the determined level of biological contamination.

* * * * *